(12) United States Patent
Kim et al.

(10) Patent No.: US 8,470,570 B2
(45) Date of Patent: Jun. 25, 2013

US008470570B2

(54) APPARATUS AND METHOD FOR PRINTING BIOMOLECULAR DROPLET ON SUBSTRATE

(75) Inventors: Kui-hyun Kim, Yongin-si (KR); Byung-chul Kim, Yongin-si (KR); Su-hyeon Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1604 days.

(21) Appl. No.: 11/684,393

(22) Filed: Mar. 9, 2007

(65) Prior Publication Data

US 2007/0264723 A1 Nov. 15, 2007

(30) Foreign Application Priority Data

Apr. 13, 2006 (KR) .................... 10-2006-0033581

(51) Int. Cl.
*C12N 13/00* (2006.01)
(52) U.S. Cl.
USPC .............. 435/173.1; 347/20; 347/44; 347/47; 347/53; 347/55
(58) Field of Classification Search
USPC .................. 347/20, 44, 47, 53, 55; 435/173.1
See application file for complete search history.

(56) References Cited

U.S. PATENT DOCUMENTS

| 4,198,643 | A * | 4/1980 | Cha et al. ........................ 347/75 |
| 2002/0003177 | A1 * | 1/2002 | O'Connor et al. ............ 239/696 |
| 2002/0168297 | A1 | 11/2002 | Shvets et al. |
| 2003/0022370 | A1 * | 1/2003 | Casagrande et al. ....... 435/372.1 |
| 2003/0040129 | A1 | 2/2003 | Shah |
| 2004/0170757 | A1 * | 9/2004 | Perrin et al. .................. 427/127 |
| 2005/0214799 | A1 * | 9/2005 | Cho et al. .......................... 435/6 |

FOREIGN PATENT DOCUMENTS

| EP | 1477809 | 11/2004 |
| KR | 1020050040162 | 5/2005 |
| KR | 1020050074496 | 7/2005 |
| WO | 0054882 | 9/2000 |
| WO | 02094442 | 11/2002 |
| WO | 2004/038449 | 5/2004 |

OTHER PUBLICATIONS

Huneiti, Z et al. Effects of conducting liquid jet disintegration on specific charge of spray. Journal of Electrostatics. 2001. 51-52: 558-564.*
Jaworek, A et al. Viscosity effect on EHD spraying using AC superimposed on DC electric field. Industry Application Conference, 2000. Conference Record of the 2000 IEEE. 2: pp. 770-776.*
Yogi, O et al. On-demand droplet spotter for preparing pico-to femtoliter droplets on surfaces. Analytical Chemistry. 2001. 73: 1896-1902.*
"Electrohydrodynamic jetting of mouse neuronal cells"; Authors: Peter A.M. Eagles, et al.; Biochemical Journal Immediate Publication. Published on Jan. 4, 2006 as manuscript BJ20051838; pp. 1-18.
"Electric field driven jetting: an emerging approach for processing living cells"; Authors: Suwan N. Jayasinghe, et al.; Biotechnol. J. 2006, 1,pp. 86-94.
"Electrohydrodynamic Jet Processing: An Advanced Electric-Field-Driven Jetting Phenomenon for Processing Living Cells"; Authors: Suwan N. Jayasinghe, et al.; Small-journal, Published online on Dec. 6, 2005, 2, No. 2, 216-219.
European Search Report for application No. 07101420.3-2104; Completion date Aug. 8, 2007.

* cited by examiner

*Primary Examiner* — Allison Ford
*Assistant Examiner* — Susan E Fernandez
(74) *Attorney, Agent, or Firm* — Cantor Colburn LLP

(57) ABSTRACT

An apparatus for printing a biomolecular droplet onto a substrate using an electric charge concentration effect includes; an electric field forming electrode including an accommodating area in which the biomolecular droplet including micro magnetic beads is accommodated and a nozzle formed on an end of the accommodating area through which the biomolecular droplet is discharged, a substrate disposed below the electric field forming electrode, including a grounded target surface onto which the biomolecular droplet discharged from the nozzle of the electric field forming electrode is deposited, a magnet disposed below the substrate which applies a magnetic force on the micro magnetic beads, and an open circuit type voltage applying unit electrically connected to the electric field forming electrode which applies a charge to the electric field forming electrode which generates an electrical force which causes the biomolecular droplet to be ejected onto the target surface of the substrate.

24 Claims, 12 Drawing Sheets

APPARATUS AND METHOD FOR PRINTING BIOMOLECULAR DROPLET ON SUBSTRATE

This application claims priority to Korean Patent application No. 10-2006-0033581, filed on Apr. 13, 2006, and all the benefits accruing therefrom under 35 U.S.C. §119, the contents of which in its entirety are herein incorporated by reference.

BACKGROUND OF THE INVENTION

1. Field of the Invention

The present invention relates to an apparatus and method for printing biomolecular droplets on a substrate, and more particularly, to an apparatus and method for printing biomolecular droplets having a small volume and diameter at a desired position.

2. Description of the Related Art

As a result of the research conducted during the Human Genome Project, there is an increasing need for methods of rapidly providing a large amount of genetic information for the diagnosis, treatment, and prevention of genetic disorders. Although the Sanger method of analyzing nucleotide sequences has been continuously improved through the development and automation of a polymerase chain reaction ("PCR") method, in which deoxyribonucleic acid ("DNA") molecules are duplicated, the Sanger method is still a complex, time consuming, labor intensive, and expensive technique which requires a lot of expertise to implement. Thus, analyzing a large number of genes using the Sanger method becomes prohibitive. As a result, new systems for analyzing nucleotide sequences are continuously being researched, and in the last few years, there have been advances in many fields relating to the manufacture and application of biochips.

A biochip is a biological microchip which includes a solid substrate made of, for example, silicon, surface-modified glass, polypropylene, or activated polyacrylamide. Biochips can be used to analyze gene developing patterns, genetic defects, protein distribution, or various kinds of reaction patterns when combined with biomolecules such as nucleic acids, proteins and cells.

If a target material to be analyzed is applied to a biochip, the target material hybridizes with probes immobilized on the biochip. The hybridization is optically or radiochemically detected and analyzed to identify the target material. For example, if a fragment of target DNA to be analyzed is applied to the DNA chip (or DNA microarray) on which probes are disposed, the target DNA complementarily hybridizes with the probes immobilized on the biochip. The hybridization is detected and analyzed using various detecting methods to identify the nucleotide sequence of the target DNA. This is known as sequencing by hybridization ("SBH").

An example of a printing apparatus for manufacturing a biochip or a DNA microarray is disclosed in Korean Patent Application No. 2005-0040162. FIG. 1 is a schematic cross-sectional view of a printing apparatus 1 disclosed in the above reference for printing biomolecular droplets on a substrate using an electrohydrodynamic phenomenon. Referring to FIG. 1, the printing apparatus 1 includes: a first electric field forming electrode 4 which is needle-shaped, formed of a conductive material, is disposed vertically, and comprises an accommodating area 2 in which a biomolecular droplet, such droplets containing nucleic acids (e.g., probe DNA, RNA, PNA, and LNA), proteins (e.g., antigen and antibody), oligopeptides, eukaryotic cells (e.g., human cells, animal cells, and vegetable cells), viruses, and bacteria, is accommodated and a nozzle 3 formed on a bottom end of the accommodating area 2 through which the biomolecular droplet is discharged; a substrate 6 disposed below the first electric field forming electrode 4, and including a target surface 5 onto which the biomolecular droplets 10 ejected from the nozzle 3 of the first electric field forming electrode 4 are deposited; and a second electric field forming electrode 7 made of a conductive material, disposed below the first electric field forming electrode 4, and attached to the substrate 6. In addition, a voltage applying device 9 is connected to and applies a voltage to the first and second electric field forming electrodes 4 and 7 via an electrode lead wire 8.

As described above, in the printing device 1, when DC and AC voltages are simultaneously applied to the first and second electric field forming electrodes 4 and 7 by driving the voltage applying unit 9, an electric field is generated between the first and second electric field forming electrodes 4 and 7 as illustrated in FIG. 2. FIG. 2 is a schematic diagram of electric field distribution formed when a voltage is applied to the printing apparatus of FIG. 1. In FIG. 2, an electric force is generated from around the biomolecular droplet 10 towards the substrate 6 due to the interaction between the electric fields generated as described above. The biomolecular droplet has a free surface, and the atmosphere may have a dielectric constant gradient. Accordingly, the biomolecular droplet 10 suspended from the nozzle 3 is ejected onto the target surface 5 of the substrate 6 by the applied electric force.

However, in another embodiment the printing device 1 can form an electric field between the first electric field forming electrode 4 and the substrate 6 when the substrate 6 is made of a conductive material or in yet another embodiment the second electric field forming electrode 7 made of a conductive material may be attached to the substrate 6, and thus, an electro-hydrodynamic effect can be generated to eject the biomolecular droplet 10. Accordingly, the substrate 6 should be made of a conductive material or in the alternative, the surface of the substrate 6 should be conductive.

As illustrated in FIG. 2, the electric field generated between the first electric field forming electrode 4 and the second electric field forming electrode 7 may not be uniform, and thus the biomolecular droplet 10 may not be ejected onto a desired position of the target surface 5 of the substrate 6.

When the distance between the first electric field forming electrode 4 and the second electric field forming electrode 7 is less than a predetermined distance, an undesirable electric discharge (also known as a spark) can be generated. Since the electric discharge may change the biochemical characteristics, size, and volume of the biomolecular droplet 10, and the surface structure or characteristics of the substrate 6, the distance between the first electric field forming electrode 4 and the second electric field forming electrode 7 should be controlled to prevent the generation of an electric discharge. For example, when the substrate 6 is coated with polymethylmethacrylate ("PMMA") and the coating thickness is 5 μm, the distance between the first electric field forming electrode 4 and the second electric field forming electrode 7 is held to more than 750 μm to prevent the generation of an electric discharge. The required distance between the first electric field forming electrode 4 and the second electric field forming electrode 7 limits the device design. In addition, when the distance between the first electric field forming electrode 4 and the second electric field forming electrode 7 is too great, it is difficult for the biomolecular droplet 10 to be ejected onto a desired position of the target surface 5 of the substrate 6.

Deposition of a sample onto a target is then a balance between avoiding electrical discharges and increasing positioning accuracy.

In order to solve such a problem in which it is difficult to eject the biomolecular droplets 10 onto a desired position of the target surface 5 of the substrate 6 while avoiding discharges, a ring-shaped electrode is introduced as a second electrode to form an electric field only within a ring. Thus, an apparatus as illustrated in FIG. 3 was developed. FIG. 3 is a schematic cross-sectional view of another conventional printing apparatus for printing biomolecular droplets on a substrate using an electrohydrodynamic phenomenon (Electric field driven jetting: an emerging approach for processing living cells, Biotechnol. J. 2006, 1, 86-94; Electric field driven jetting: Electrohydrodynamic Jet Processing: An Advanced Electric-Field-Driven Jetting Phenomenon for Processing Living Cells Small. 2006, 2, No. 2, 216-219; Electrohydrodynamic jetting of mouse neuronal cells, Biochemical journal, 2006 Jan. 4). Referring to FIG. 3, when biomolecular droplets are ejected out of an electric spray needle, which corresponds to a first electrode as described above, by an electric field formed with a ring-shaped electrode, which corresponds to a second electrode as described above, biomolecular droplets are ejected only within the ring-shaped electrode and reach the target surface. However, although biomolecular droplets are ejected into only within the ring-shaped electrode, the ring-shaped electrode must be separated from the electric spray needle by a predetermined distance in order to prevent an electrical discharge from being generated. Thus, the biomolecular droplets still can not be consistently ejected onto a desired position of a substrate.

To solve the problems of printing biomolecular droplets using an electrohydrodynamic effect, an apparatus 100a for printing biomolecular droplets as illustrated in FIG. 4 using an electric charge concentration effect was disclosed in Korean Patent Application No. 2005-74496. In the apparatus 100a, when an open circuit type voltage applying unit 60a simultaneously applies DC and AC voltages to an electric field forming electrode 20a after biomolecular droplets are first supplied to an accommodating area 22a, positive charges migrate into the biomolecular droplets 10a (not shown in FIG. 4, but shown in FIG. 5) which are suspended from a nozzle 23a, and thereby negative charges are induced along a target surface 31a in a substrate 30a which is grounded.

An electric field is formed between the positive charges and the negative charges as illustrated in FIG. 5. Accordingly, when positive charges migrate into the biomolecular droplets 10a, thereby inducing negative charges in a portion of the substrate 30a disposed opposite the biomolecular droplet 10a, a force is generated between the positive charges and the negative charges. Here, the negative charges are induced below the biomolecular droplet 10a, so that the force is concentrated on the bottom of the biomolecular droplet 10a. The biomolecular droplet 10a suspended from the nozzle 23a is ejected onto the substrate 30a due to the force as illustrated in the fourth photo of FIG. 6, and as illustrated in the schematic representation shown in FIG. 7, and is thus converted to an approximately jar shaped biomolecular droplet. A neck is formed in the jar-shaped biomolecular droplet 10a.

Accordingly, when the biomolecular droplet 10a suspended from the nozzle 23a is ejected onto the substrate 30 and then formed as illustrated in FIG. 7, the positive charge in the biomolecular droplet 10a is cancelled by the negative charge formed on the substrate 30a, resulting in a reduction in force. That is, the force which causes the biomolecular droplet 10a suspended from the nozzle 23a to be ejected is decreased after the droplet 10a contacts the target area on the substrate. In addition, a surface tension A between the neck-shaped biomolecular droplet 10a and the substrate 30a, and a surface tension B between the neck-shaped biomolecular droplet 10a and the electric field forming electrode 20a act in directions opposite to each other as illustrated in FIG. 7. Accordingly, when the positive charge in the biomolecular droplet 10a is cancelled, the force is decreased and the surface tensions A and B also act opposite to each other. Thus, due to the force of the surface tensions, the biomolecular drop 10a is separated at the neck-shaped portion to become two biomolecular droplets.

Accordingly, the biomolecular droplets are deposited on the substrate 30a as illustrated in the last photo of FIG. 6. In the apparatus 100a, the substrate 30a is grounded. Thus, the substrate 30a can be made of any material. In addition, negative charges can be induced on a portion of the substrate 30a disposed opposite to the biomolecular droplet 10a by the positive charges in the biomolecular droplet 10a, and since a larger amount of positive charge is developed in the biomolecular droplet 10a as compared to when an electrohydrodynamic effect is used, the biomolecular droplet 10a can be ejected and deposited on a desired position of substrate 30a.

In addition, a very high force acts so that the biomolecular droplet 10a can be printed with a smaller size and volume than those of the biomolecular droplet in the prior art. Also, the substrate 30a is grounded, thereby electric discharge is not generated unlike when an electrohydrodynamic effect is used as in the prior art. Accordingly, a distance between the electric field forming electrode 20a and the substrate 30a can be freely adjusted. That is, in the apparatus 100a for printing biomolecular droplets disclosed in Korean Patent Application No. 2005-74496, it is possible that biomolecular droplets having a small size and volume are printed on a desired position using an electric charge concentration effect.

However, to manufacture a biochip having a high density, a method of printing biomolecular droplets having an even smaller volume is required. In particular, in order to conduct research into the interaction of cells, including stem cells, the printing of biomolecular droplets having a volume as small as 6 or fewer cells per biomolecular droplet are required. The size of the required biomolecular droplet varies depending on a concentration of cells, but, for example, when 3% of a glycerol medium solution having a concentration of $3 \times 10^6$ cells/ml is to be printed, a biomolecular droplet having a diameter of 60 μm or less is required.

Therefore, a method of printing biomolecular droplets having a smaller volume and diameter using the device for printing biomolecular droplets disclosed in Korean Patent Application No. 2005-74496 is desired.

BRIEF SUMMARY OF THE INVENTION

The present invention provides an apparatus for printing biomolecular droplets having a small volume and diameter on a desired position of a substrate.

The present invention also provides a method of printing biomolecular droplets having a small diameter and volume on a desired position of a substrate.

According to an exemplary embodiment of the present invention, an apparatus for printing a biomolecular droplet onto a substrate using an electric charge concentration effect, the apparatus including; an electric field forming electrode includes an accommodating area in which the biomolecular droplet comprising micro magnetic beads is accommodated and a nozzle formed on an end of the accommodating area through which the biomolecular droplet is discharged, a substrate disposed below the electric field forming electrode, comprises a grounded target surface onto which the biomolecular droplet discharged from the nozzle of the electric field forming electrode is deposited, a magnet disposed below the substrate which applies a magnetic force on the micro magnetic beads, and an open circuit type voltage applying unit electrically connected to the electric field forming electrode which applies a charge to the electric field forming electrode which generates an electrical force which causes the biomolecular droplet to be ejected onto the target surface of the substrate.

In one exemplary embodiment the magnet is disposed adjacent to a lower surface of the substrate.

In one exemplary embodiment the micro magnetic bead may have a diameter of about 100 nm to about 15,000 nm, and a concentration in the range of about $10^4$ beads/ml to about $10^{12}$ beads/ml.

In one exemplary embodiment the biomolecules can be selected from the group consisting of nucleic acids, proteins, oligopetides, saccharides, eukaryotic cells, stem cells, viruses and bacteria.

In one exemplary embodiment the biomolecular droplet printed on the substrate has a diameter of about 60 μm or less.

In one exemplary embodiment the apparatus for printing the biomolecular droplet further includes a printer body which supports the electric field forming electrode.

In one exemplary embodiment the electric field forming electrode and the open circuit type voltage applying unit are electrically connected to an electrode lead wire which is connected to a top end of the electric field forming electrode.

In one exemplary embodiment the open circuit type voltage applying unit can simultaneously apply the AC voltage or the DC voltage to the electric field forming electrode.

In one exemplary embodiment the DC voltage is in the range of about 5 V to about 100,000 V and the AC voltage in the range of about 5 V to about 100,000 V.

In one exemplary embodiment the DC voltage is in the range of about 500 V to about 10,000 V and the AC voltage in the range of about 500 V to about 10,000 V.

In one exemplary embodiment the AC voltage has a frequency of about 10 Hz to about 1,000 Hz.

In one exemplary embodiment the DC voltage has a voltage of about 2,000 V and the AC voltage having a voltage of about 500 V and a frequency of about 130 Hz.

In one exemplary embodiment the substrate may be made of at least one selected from the group consisting of silicon, glass and polymer.

In one exemplary embodiment a surface of the substrate is coated with at least one selected from the group consisting of an amine group, a carboxyl group, biotin, streptavidine, poly-L-lysine and thiol.

In one exemplary embodiment the substrate comprises a planar part, and a plurality of protrusions protruding upwards from the planar part.

In one exemplary embodiment the substrate is disposed below and substantially perpendicular to the electric field forming electrode.

In one exemplary embodiment the electric field forming electrode is made of at least one selected from the group consisting of a conductive metal, a conductive polymer and indium tin oxide ("ITO") glass.

In one exemplary embodiment at least a portion of the nozzle of the electric field forming electrode is hydrophobically treated.

In one exemplary embodiment the apparatus further includes; a plurality of the electric field forming electrodes arranged with substantially the same pitch, and a plurality of target surfaces arranged on the substrate, wherein the target surfaces are disposed with the electric field forming electrodes are disposed to corresponded to the electric field forming electrodes.

According to another exemplary embodiment of the present invention, there is provided a method of printing a biomolecular droplet on a substrate using an electric charge concentration effect, the method including; disposing an electric field forming electrode including an accommodating area in which the biomolecular droplet including micro magnetic beads is accommodated and a nozzle formed at an end of the accommodating area through which the biomolecular droplet is discharged above the substrate, disposing the substrate below the electric field forming electrode, wherein the substrate is grounded and includes a target surface onto which the biomolecular droplet discharged from the nozzle of the electric field forming electrode is deposited, disposing a magnet which applies a magnetic field to the micro magnetic beads below the substrate, electrically connecting an open circuit type voltage applying unit which is electrically connected to the electric field forming electrode, supplying the biomolecular droplet including micro magnetic beads to the accommodating area of the electric field forming electrode, and ejecting the biomolecular droplet onto the target area when the open circuit type voltage applying unit applies a voltage to the electric field forming electrode.

In one exemplary embodiment the method can further include culturing cells adherently on the substrate after the biomolecular droplet is ejected, removing the magnet, removing micro magnetic beads by washing the adherently cultured cells; and adding a fresh medium onto the adherently cultured cells.

BRIEF DESCRIPTION OF THE DRAWINGS

The above and other aspects, features and advantages of the present invention will become more apparent by describing in more detail exemplary embodiments thereof with reference to the attached drawings in which.

DETAILED DESCRIPTION OF THE INVENTION

Figure 1:
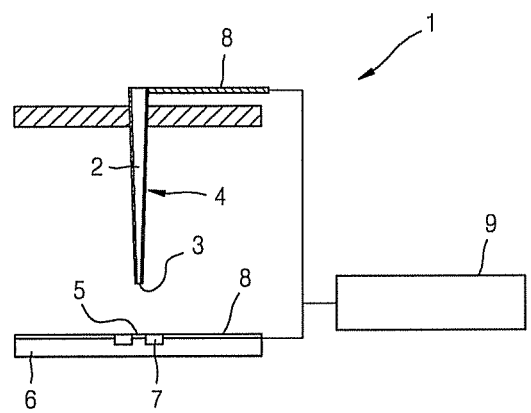
FIG. 1 is a schematic cross-sectional view of a conventional printing apparatus using an electrohydrodynamic phenomenon.
Figure 2:
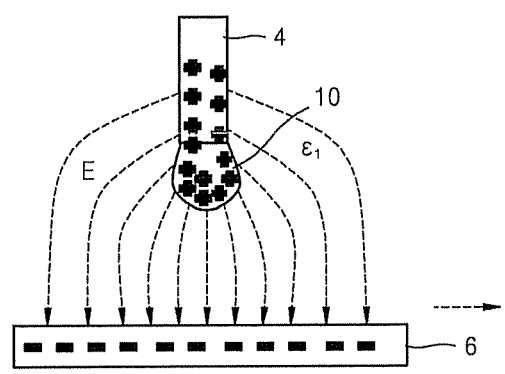
FIG. 2 is a schematic diagram of an electric field distribution formed when a voltage is applied to the printing apparatus of FIG. 1.
Figure 3:
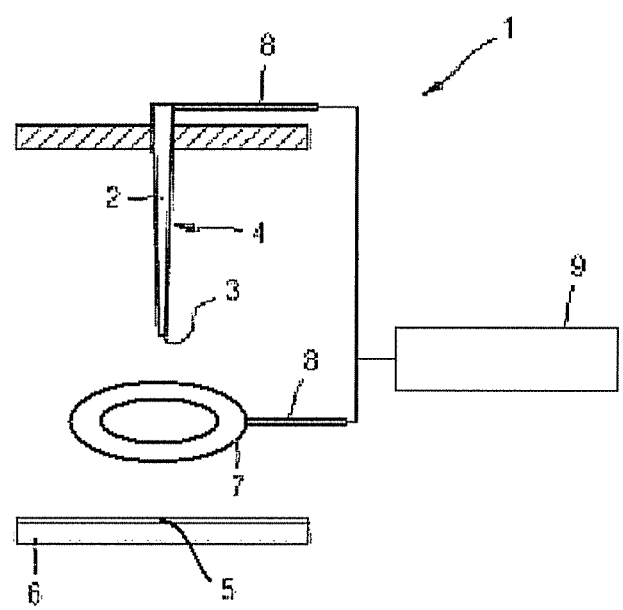
FIG. 3 is a schematic cross-sectional view of another conventional printing apparatus using an electrohydrodynamic phenomenon.
Figure 4:
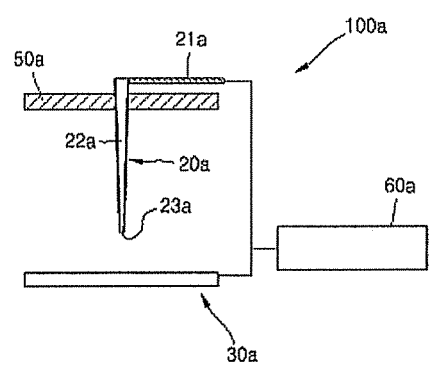
FIG. 4 is a schematic cross-sectional view of another conventional printing apparatus.
Figure 5:
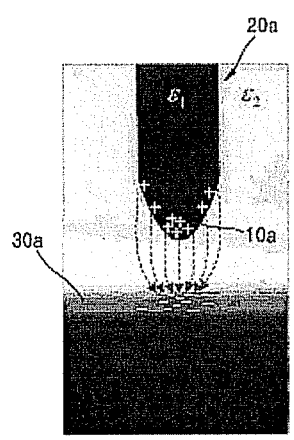
FIG. 5 is a diagram illustrating the distribution of positive charges applied in an electric field forming electrode and negative charges induced by the positive charges, and a force applied to a biomolecular droplet suspended from a nozzle when a voltage is applied to the printing device of FIG. 4.
Figure 6:
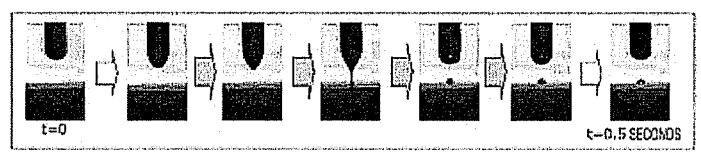
FIG. 6 is a diagram illustrating a process of printing biomolecular droplets using the printing apparatus of FIG. 4.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will be described more fully with reference to the accompanying drawings, in which exemplary embodiments of the present invention are shown.

Figure 8:
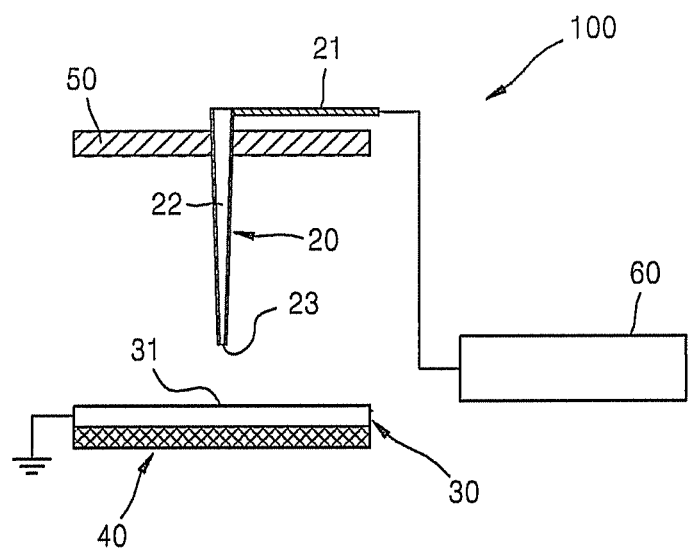
FIG. 8 is a schematic cross-sectional view of an exemplary embodiment of a printing device according to the present invention.
Figure 9:
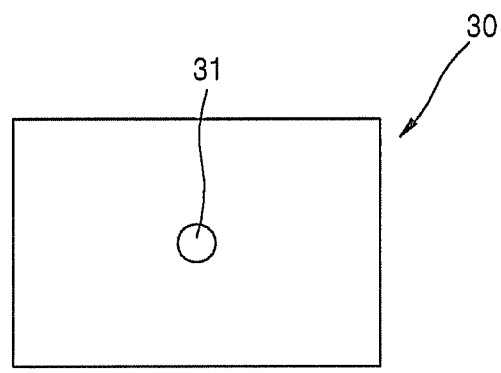
FIG. 9 is a top plan view of a substrate of the exemplary embodiment of a printing device of FIG. 8, according to the present invention.
Figure 10A:
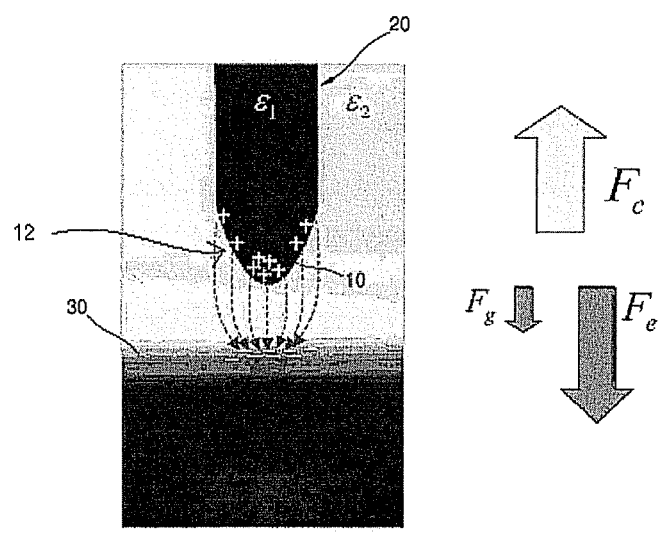
FIG. 10A is a schematic illustration of the distribution of positive charges in an electric field forming electrode and negative charges induced by the positive charges, and a force applied to a biomolecular droplet suspended from a nozzle when a voltage is applied to the exemplary embodiment of a printing device of FIG. 8, according to the present invention.
Figure 10B:
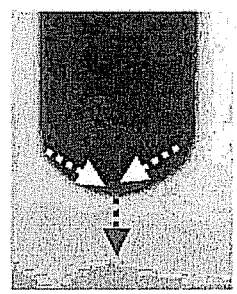
FIG. 10B is a schematic illustration of micro magnetic beads included in the biomolecular droplet suspended from the nozzle of the exemplary embodiment of a printing device illustrated in FIG. 8.

FIG. 8 is a schematic cross-sectional view of an exemplary embodiment of a printing device 100 for printing a biomolecular droplet 10 according to the present invention, FIG. 9 is a top plan view of a substrate 30 of the exemplary embodiment of a printing device 100 of FIG. 8, FIG. 10A is a schematic illustration of the distribution of positive charges in an electric field forming electrode 20 of the exemplary embodiment of a printing device 100 of FIG. 8 and negative charges induced by the positive charges, and a force applied to the biomolecular droplet 10 suspended from a nozzle 23 of the electric field forming electrode 20 when a voltage is applied to the exemplary embodiment of a printing device 100 of FIG. 8 according to the present invention, and FIG. 10B is a schematic illustration of micro magnetic beads included in the biomolecular droplet 10 suspended from the nozzle of the electric field forming electrode 20 of the exemplary embodiment of a printing device 100 illustrated in FIG. 8 are concentrated at a lower portion of the biomolecular droplet 10 by micro magnetic beads being attracted towards the substrate due to a magnetic force generated by a magnet.

Figure 11:
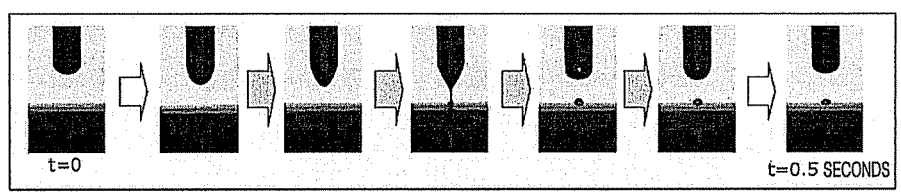
FIG. 11 is a diagram illustrating an exemplary embodiment of a process of printing a biomolecular droplet using the exemplary embodiment of a printing device of FIG. 8, according to the present invention.
Figure 12:
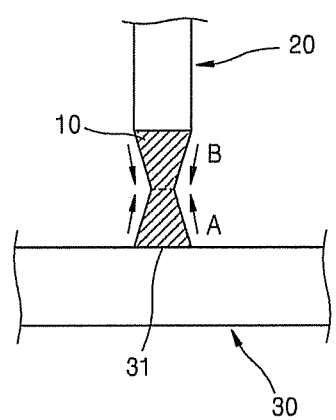
FIG. 12 is a diagram illustrating how surface tension affects a biomolecular droplet ejected onto the substrate in the exemplary embodiment of a printing device of FIG. 8, according to the present invention.

FIG. 11 illustrates a process of printing a biomolecular droplet using the exemplary embodiment of a printing device 100 of FIG. 8, according to the present invention. FIG. 12 is a diagram illustrating how surface tension affects a biomolecular droplet having a neck shape when the biomolecular droplet is ejected onto the substrate 30 of the exemplary embodiment of a printing device 100 of FIG. 8, according to the present invention.

Referring to FIGS. 8 through 12, the printing device 100 for printing the biomolecular droplet 10 includes the electric field forming electrode 20, the substrate 30, a magnet 40, a printer body 50, and an open circuit type voltage applying unit 60.

The electric field forming electrode 20 is made of a conductive metal, exemplary embodiments of which include gold, platinum, copper, and various other similar materials, a conductive polymer, indium tin oxide ("ITO"), glass, and carbon nanotubes, or at least two selected therefrom. In the present exemplary embodiment, the electric field forming electrode 20 is made of gold. The electric field forming electrode 20 is shaped like a needle and extends vertically. An electrode lead wire 21 is connected to a top end of the electric field forming electrode 20. The electric field forming electrode 20 is electrically connected to the open circuit type voltage applying unit 50 via the electrode lead wire 21.

The electric field forming electrode 20 includes an accommodating area 22 and the nozzle 23.

The biomolecular droplet 10 comprising micro magnetic beads and biomolecules such as nucleic acids (e.g., probe DNA, RNA, peptide nucleic acid ("PNA"), and locked nucleic acid ("LNA")), proteins (e.g., antigen and antibody), oligopeptide, saccharide, a eukaryotic cells (e.g., human cells, animal cells, and vegetable cells), viruses, and bacteria are accommodated in the accommodating area 22. It is preferable that the micro magnetic beads are smaller than the biomolecules to be used in order for the biomolecules to be printed smoothly. In one exemplary embodiment the micro magnetic beads have a diameter of about 100 nm to about 15 μm, and in another exemplary embodiment they have a diameter of about 1 μm to about 3 μm. In one exemplary embodiment the micro magnetic beads included in the biomolecular droplet 10 have a concentration of about $1 \times 10^4$ beads/ml to about $1 \times 10^{12}$ beads/ml. In yet another exemplary embodiment the concentration of the micro magnetic beads in the biomolecular droplets is about $10^8$ beads/ml-to about $10^9$ beads/ml. Such micro magnetic beads can be any micro magnetic beads which can be induced by magnetic force. In the present exemplary embodiment, the magnetic force is formed by a magnet disposed on a lower portion of the substrate 30. The magnetic force is provided in the direction of the substrate. One exemplary embodiment of the micro magnetic beads are commercially available Dynabeads® (Dynal), or various other micro magnetic beads.

The nozzle 23 is formed on the bottom end of the accommodating area 22. The inner diameter of the nozzle 23 is very small, and thus surface tension of the biomolecular droplet 10 can suspend the biomolecular droplet 10 in the nozzle 23 against gravity until a force is applied from outside. The biomolecular droplet 10, which contains both biomolecules and micro magnetic beads, accommodated in the accommodating area 22 can be discharged from the accommodating area 22 via the nozzle 23 by an electric charge concentration effect, which will be described later. The area around the nozzle 23 is hydrophobic-treated so that the contact angle between the biomolecular droplet 10 and the surface of the nozzle 23 is large enough to prevent the biomolecular droplet 10 from flowing outwards.

In one exemplary embodiment, the substrate 30 is a substrate for culturing cells. Alternative exemplary embodiments include configurations wherein the substrate 30 is a biochip or a DNA microarray, or various other similar components. Exemplary embodiments of the substrate 30 are made of silicon, glass, polymer, or at least two selected therefrom. In the present exemplary embodiment, the substrate 30 is made of glass. The substrate 30 is disposed substantially perpendicular to the electric field forming electrode 20 and disposed below the electric field forming electrode 20, and a target surface 31 is formed on the substrate 30. The biomolecular droplet 10 discharged via the nozzle 23 of the electric field forming electrode 20 is ejected and deposited on the target surface 31. In the present exemplary embodiment the substrate 30 is grounded. In one exemplary embodiment the surface of the substrate 30, in particular, the target surface 31 of the substrate 30, is coated using any one or at least two materials selected from the group consisting of an amine group, a carboxyl group, streptavidine, biotin, thiol, and poly-L-lysine.

The magnet 40 can be disposed on the bottom of the substrate 30, allowing micro magnetic beads included in the biomolecular droplet 10 to be attracted by a magnetic force towards the substrate 30. In the present exemplary embodiment the magnet 40 is disposed adjacent to the lower surface of the substrate 30 as illustrated in FIG. 8. The magnet 40 exerts a magnetic force on the micro magnetic beads included in the biomolecular droplet 10 accommodated in the accommodating area 22 of the electric field forming electrode 20, and thereby the micro magnetic beads are attracted by the magnetic force towards a top surface of the substrate 30, enabling micro magnetic beads in the biomolecular droplet 10 suspended from the nozzle 23 to be concentrated at a lowest point of the biomolecular droplet 10. Due to such a phenomenon, an apparatus for printing a biomolecular droplet according to an embodiment of the present invention enables a biomolecular droplet having a smaller size and volume to be printed.

The magnet 40 can be any magnet which can attract micro magnetic beads by a magnetic force.

The printer body 50 is disposed above the nozzle 23 of the electric field forming electrode 20. The printer body 50 supports the electric field forming electrode 20, and in one exemplary embodiment is made of polymethlymethacrylate ("PMMA"). In one exemplary embodiment the printer body 50 can be moved three-dimensionally along x-, y-, and z-axes by a separate driving device (not illustrated). The electric field forming electrode 20 supported by the printer body 50 can be moved to be disposed above the target surface 31 of the substrate 30 and separated from the target surface 31 by a predetermined distance by driving the separate driving device.

The open circuit type voltage applying unit 60 is electrically connected to the electric field forming electrode 20. The open circuit type voltage applying unit 60 can simultaneously apply DC and AC voltages to the electric field forming electrode 20 via the electrode lead wire 21.

Due to the simultaneous application of the DC and AC voltages, positive charges migrate into the biomolecular droplet 10 suspended from the nozzle 23 and negative charges are induced in the substrate 30 due to those positive charges. Accordingly, an electric field is formed between the positive and negative charges, as illustrated in FIG. 10A. The biomolecular droplet 10 is attracted towards the target surface 31 of the substrate 30 due to the force generated between the positive charges applied in the electric field forming electrode 20 and the negative charges induced by the positive charges in the substrate 30. In addition, the micro magnetic beads included in the biomolecular droplet 10 are attracted towards the substrate 30 due to the electrical force generated between them and the substrate 30 in addition to the magnetic force provided by the magnet 40 adjacent to a lower surface of the substrate 30, and thus the micro magnetic beads included in the biomolecular droplet 10 suspended from the nozzle 23 of the electric field forming electrode 20 are concentrated at a lower portion of the biomolecular droplet 10. As a result, the biomolecular drop 10 is tapered, enabling the biomolecular droplet 10 to be printed with a smaller size and volume. This will be described in greater detail below.

Referring to FIG. 10A, the distribution of positive charges in the electric field forming electrode 20 and the negative charges induced by the positive charges, and a force applied to the biomolecular droplet 10 suspended from the nozzle 23 when a voltage is applied to the exemplary embodiment of a printing device 100 of FIG. 8 is illustrated. For convenience of description the magnetic force applied to the micro magnetic beads included in the biomolecular droplet 10 by the magnet 40 disposed on the bottom of the substrate 30 has been excluded. Referring to FIG. 10A, when a voltage is applied to the electric field forming electrode 20, a collection of forces act on the biomolecular droplet 10 suspended from the nozzle 23. The forces are gravity ($F_g$), surface tension ($F_c$), and the electrical force ($F_e$) between the positive charges in the biomolecular droplet 10 and the induced negative charges in the substrate 30. Equation 1 describes the relationship between the abovementioned forces at the time prior to the ejection of the droplet 10.

$$(F_g)+(F_e)=(F_c) \qquad \text{Equation (1)}$$

where $F_g=\rho g \Delta V^{drop}$ ($\rho$ is the density of the biomolecular droplet 10, g is acceleration of gravity, and $\Delta V^{drop}$ is the volume of the biomolecular droplet 10 suspended from the nozzle 23), $F_c=2\pi R\gamma$ (R is the radius of the nozzle 23 and $\gamma$ is the surface tension of the biomolecular droplet 10 per unit length, and $F_e=\rho_f E-E^2\in_r/2$ ($\rho_f$ is the free charge of the biomolecular droplet 10, E is the magnitude of the electric field, $\in_r \nabla$ is the dielectric constant). The electric force is the sum of an electrophoretic force ($\rho_f E$) and a dielectrophoretic force ($-E^2\nabla\in/2$).

In Equation 1, gravity ($F_g$) is proportional to the volume of the biomolecular droplet 10 suspended from the nozzle 23, however, the volume of the biomolecular droplet 10 is sufficiently small that the force of gravity may be effectively ignored in Equation 1.

Thus, when the force ($F_e$) becomes greater than the surface tension ($F_c$) of the biomolecular droplet 10 suspended from the nozzle 23, the equilibrium of the forces is not maintained, and the downward force ($F_e$) overcomes the mainly upward force of the surface tension ($F_c$) such that the biomolecular droplet 10 is ejected onto the target surface 31 of the substrate 30. In addition, the charges concentrated in the lower portion of the biomolecular droplet 10 suspended from the nozzle 23 induce counter-charges on a portion of the substrate 30 which is below the biomolecular droplet 10. Therefore, the force ($F_e$) is generated between the charges in the biomolecular droplet 10 and the counter-charges induced in the substrate 30.

As described above, the biomolecular droplet 10 is ejected onto the surface of the substrate 30 due to the force generated by the electric charge concentration effect. In addition the biomolecular droplet 10 suspended from the nozzle 23 is subject to a magnetic force generated by the magnet 40 adjacent to a lower surface of the substrate 30 as illustrated in FIG. 10B. Due to such a magnetic force, the micro magnetic beads are concentrated with the biomolecules at a lowest point 12 of the biomolecular droplet 10. Accordingly, a lower portion of the biomolecular droplet 10 suspended from the nozzle 23 has a narrower width compared to when micro magnetic beads are not used. When the lower portion of the biomolecular droplet 10 becomes narrower, the volume of biomolecular droplets 10 printed on the target surface 31 of the substrate 30 can be a lot smaller, and thus a biomolecular droplet having higher density can be printed on the substrate 30.

Meanwhile, a DC voltage ranging from about 5 V to about 100,000 V and an AC voltage ranging from about 5 V to about 100,000 V and having a frequency of about 10 Hz to about 1,000 Hz may be simultaneously applied to the electric field forming electrode 20 by the open circuit type voltage applying unit 50. In one exemplary embodiment the DC voltage ranges from about 500 V to about 10,000 V and an AC voltage ranging from about 500 V to about 10,000 V and having a frequency ranging from about 10 Hz to about 1,000 Hz may be applied. When the DC voltage and the AC voltage are outside these ranges, the biomolecular droplet 10 is not efficiently ejected on the substrate 30 because the force acting on the biomolecular droplet 10 is of a sufficient magnitude to effectively overcome the force of the surface tension ($F_c$). In another exemplary embodiment the DC voltage is about 2,000 V, and the AC voltage is about 500 V and has a frequency of about 130 Hz.

Hereinafter, a method of printing the biomolecular droplet 10 onto the substrate 30 using the exemplary embodiment of a printing device 100 which utilizes the electric charge concentration effect will be described in more detail with reference to FIG. 11, according to the present invention.

First, the driving device is driven to move the printer body 50, which supports the electric field forming electrode 20, above the target surface 31 of the substrate 30. Thereafter, the biomolecular droplet 10 comprising micro magnetic beads and biomolecules is supplied to the accommodating area 22 of the electric field forming electrode 20. At this time, the electric field forming electrode 20 includes the nozzle 23 formed on the bottom thereof, however, the inner diameter of the nozzle 23 of the electric field forming electrode 20 is very small, and thus the biomolecular droplet 10 is suspended from the nozzle 23. The force of surface tension ($F_c$) on the biomolecular droplet 10 is sufficient to overcome the force of gravity ($F_g$).

After the biomolecular droplet 10 is supplied to the accommodating area 22 as described above, the open circuit type voltage applying unit 60 simultaneously applies a DC voltage ranging from about 5 V to about 100,000 V and an AC voltage ranging from about 5 to about 100,000 V with a frequency of about 10 Hz to about 1,000 Hz to the electric field forming electrode 20. As a result, positive charges migrate into the biomolecular droplet 10 suspended from the nozzle 23, and thus negative charges are induced in the substrate 30, which is grounded. Accordingly, an electric field is generated between the positive charges and the negative charges, as illustrated in FIG. 1A.

Accordingly a force is generated between the positive charges and the negative charges. Here, the negative charges are induced below the biomolecular droplet 10, so that the force is concentrated on the bottom of the biomolecular droplet 10. In addition, micro magnetic beads 11 included in the biomolecular droplet 10 receive a magnetic force generated by a magnet adjacent to a lower surface of the substrate 30, and thus the micro magnetic beads 11 included in the biomolecular droplet 10 suspended from the nozzle 23 are concentrated at a lower portion of the biomolecular droplet 10, so that the biomolecular droplet 10 becomes tapered.

Figure 7:
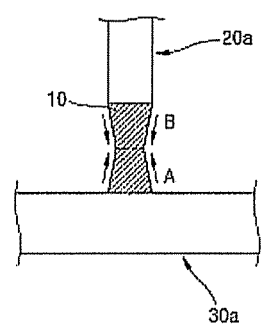
FIG. 7 is a diagram illustrating surface tension affecting a biomolecular droplet having a neck shape when the biomolecular droplet is ejected onto the substrate in the printing device of FIG. 4.

Accordingly, the biomolecular droplet 10 suspended from the nozzle 23 having a narrow lower portion is ejected onto the substrate 30 by the force generated by the electric charge concentration as illustrated the middle photo of FIG. 11 and in FIG. 12, and is thus converted to an approximately jar shaped biomolecular droplet, including a neck formed in the jar-shaped biomolecular droplet. Accordingly, the biomolecular droplet 10 suspended from the nozzle 23 is ejected onto the substrate 30 and then formed as illustrated in FIG. 12, and thus the positive charge in the biomolecular droplet 10 is cancelled by the negative charge in the substrate 30, resulting in a reduction in the force generated by the electric charge concentration. That is, the force that attracts the biomolecular droplet 10 suspended from the nozzle 23 towards the substrate 30 is decreased. In addition, a surface tension A between the neck-shaped biomolecular droplet 10 and the substrate 30, and a surface tension B between the neck-shaped biomolecular droplet 10 and the electric field forming electrode 20 act opposite to each other as illustrated in FIG. 12. Accordingly, when the positive charge in the biomolecular droplet 10 is cancelled, a force generated by the electric charge concentration is decreased, and thus the biomolecular drop 10 becomes separated at a neck-shaped portion of the biomolecular drop 10 into two biomolecular droplets. Accordingly, the biomolecular droplets are ejected and deposited on the substrate 30 as illustrated in the last photo of FIG. 11. During this procedure, a lower portion of the biomolecular droplet 10 suspended from the nozzle 23 becomes narrower due to the presence of the micro magnetic beads, so that a volume of the jar-shaped biomolecular droplet 10 is smaller and a neck portion of the jar-shaped biomolecular droplet 10 is narrower than in a conventional droplet such as illustrated in FIG. 7. Therefore, a biomolecular droplet having a smaller volume can be printed on the substrate 30 compared to when micro magnetic beads are not utilized.

Figure 13:
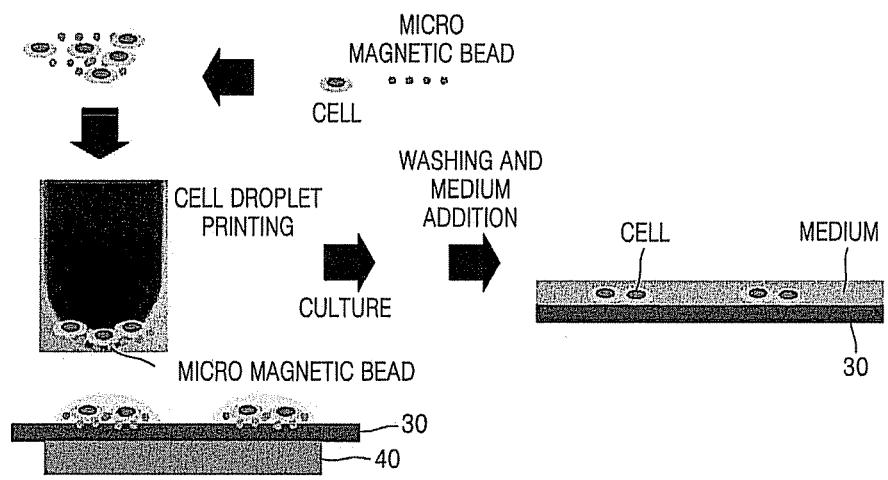
FIG. 13 is a diagram illustrating an exemplary embodiment of processes of removing magnetic beads after cells are adherently cultured in a substrate, when cell droplets are printed using the exemplary embodiment of a printing device of FIG. 8, according to the present invention.

The micro magnetic beads included in the biomolecular droplet 10 printed on the top surface of the substrate 30 according to current embodiment of the present invention can be removed by any of several well known methods or the biomolecular droplet can be used without their removal. For example, when a biomolecular droplet comprising biomolecules such as cells is printed, biomolecular droplets are printed on the substrate 30 and then cells are adherently cultured in the substrate 30, and then the magnet 40 adjacent to a lower surface of the substrate 30 is removed. Then, the printed and adherently cultured cells are washed to remove the micro magnetic beads which are included in the biomolecular droplet, and are printed on the substrate 30 with the biomolecule. The micro magnetic beads can be removed by adding a fresh culture. These processes are briefly described in FIG. 13.

Experiments were performed using an exemplary apparatus for printing a biomolecular droplet according to the present invention and a conventional apparatus not utilizing a magnet or micro magnetic bead.

EXPERIMENT 1

Figure 14:
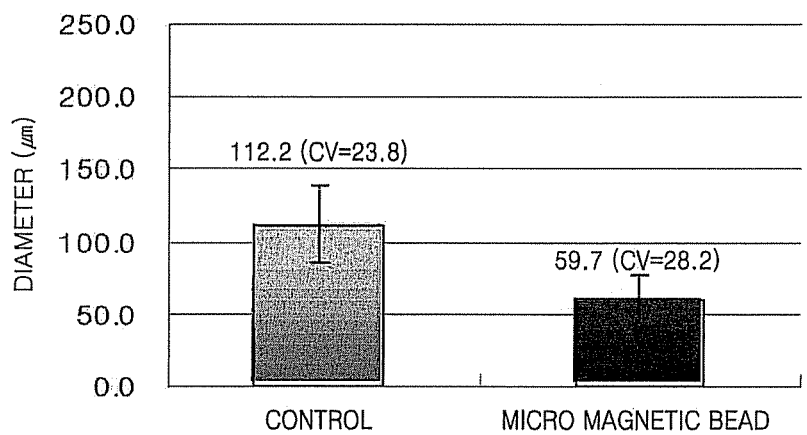
FIG. 14 is a graph comparing average diameter values of printed biomolecular droplets, with and without magnetic beads, using the exemplary embodiment of a printing device of FIG. 8, according to the present invention.

A biomolecular droplet comprising 3% of an aqueous glycerol solution including $6.7 \times 10^8$ beads/ml of Dynabeads and M-280 streptavidin (2.8 µm) was used to fill an accommodating area of an electric field forming electrode. A control solution of 3% of an aqueous glycerol solution was prepared to provide a comparison result. An electric field forming electrode having a diameter of 0.46 mm and a substrate made of glass were prepared. An electric field of 3 kV and 4 kHz was applied to the electric field forming electrode to measure a diameter of the biomolecular droplet ejected onto the substrate. Such a process was repeated 30 times to calculate an average diameter and a coefficient of variation ("CV") of a biomolecular droplet ejected onto the substrate. The results are shown in FIG. 14. As shown in FIG. 14, when a micro magnetic bead is introduced, an average diameter of the printed biomolecular droplet is 59.7 µm and the coefficient of variation of the printed biomolecular droplet is 28.2, and in the case of a control, an average size of the printed biomolecular droplet is 112.2 µm and the coefficient of variation of the printed biomolecular droplet is 23.8. Therefore an exemplary embodiment of an apparatus in which a micro magnetic bead and magnet are included print a biomolecular drop having a smaller size compared to a comparative apparatus.

Example 2

Next, to confirm whether an exemplary embodiment of an apparatus for printing the biomolecular droplet according to the present invention as described above can print 6 or fewer cells when using cells as a biomolecule, the following experiment was performed using the exemplary apparatus for printing the biomolecular droplet used in the above experimental example.

A biomolecular droplet comprising 3% of an aqueous glycerol solution including $3 \times 10^6$ cells/ml of HeLa cell (ATCC® Number: CCL-2) and $3.4 \times 10^8$ beads/ml of Dynabeads M-280 streptavidin (2.8 µm) was used as a biomolecular droplet to fill an accommodating area of the electric field forming electrode. A control droplet was prepared in the same manner as above, except that Dynabeads M-280 streptavidin was not added to the biomolecular droplet. A substrate made of glass was also prepared. An AC voltage of 3 kV and having a frequency of 4 kHz was applied to the electric field forming electrode to print the biomolecular droplet on the substrate.

Figure 15:
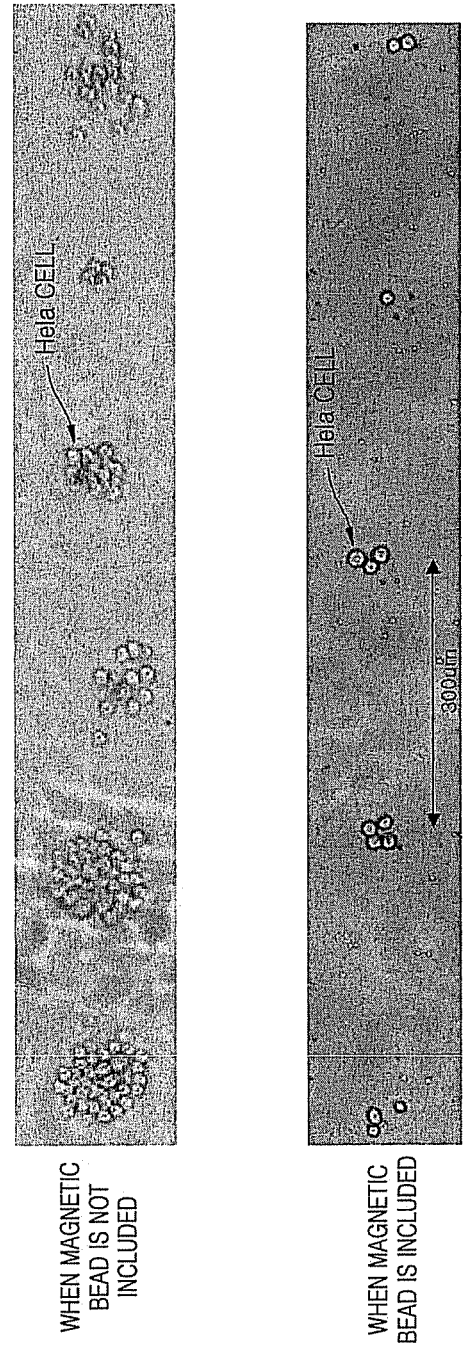
FIG. 15 compares microscopic images of cell droplets, with and without magnetic beads, printed on the substrate of the exemplary embodiment of a printing device of FIG. 8, using the exemplary embodiment of a printing device of FIG. 8, according to the present invention.

Results of observing the biomolecular droplet printed on the substrate are shown in FIG. 15. As shown in FIG. 15, in the case of a control droplet, which does not utilize a magnetic bead, the number of printed HeLa cells is greater than 20. However, when a micro magnetic bead is included, the number of cells in the printed biomolecular droplet is 4 or less. Therefore the exemplary embodiment of an apparatus for printing a molecular droplet according to the present invention including a micro magnetic bead and magnet enables the printed biomolecular droplet to contain fewer cells.

Example 3

Next, a comparison was performed using a non-magnetic micro bead and the exemplary embodiment of a micro magnetic bead according to the present invention. The following experimental example was performed using the exemplary embodiment of an apparatus for printing the biomolecular droplet used in the previous examples described above.

A biomolecular droplet comprising 3% of an aqueous glycerol solution including $6.7 \times 10^8$ beads/ml of Dynabeads M-280 streptavidin (diameter: 2.8 µm), 3% of an aqueous glycerol solution, 3% of an aqueous glycerol solution including $6.7 \times 10^8$ beads/ml of a silicon bead (diameter 3.0 µm) was used to fill the accommodating area of the electric field forming electrode. When the silicon bead was included, experiments were performed when the magnet was included and excluded respectively.

Figure 16:
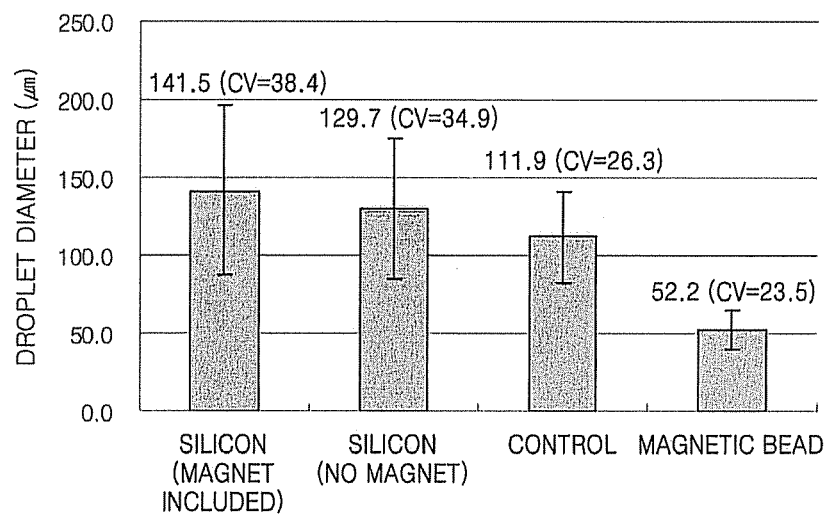
FIG. 16 is a graph showing average diameter values of biomolecular droplets printed on the substrate of the exemplary embodiment of a printing apparatus of FIG. 8, when silicon microbeads, a magnetic bead, or a no microbead are utilized in the exemplary embodiment of a printing apparatus of FIG. 3, according to the present invention.

A substrate made of glass was prepared, and an AC voltage of 3 kV and having a frequency of 4 kHz was applied to the electric field forming electrode to measure a diameter of the biomolecular droplet ejected onto the substrate. Such an experiment was repeated 40 times to calculate an average diameter and a coefficient of variation CV) of the biomolecular droplet ejected onto the substrate. The results are shown in FIG. 16. As shown in FIG. 16, in the case of a silicon bead, when a magnet is used, an average diameter of the printed biomolecular droplet is 141.5 µm and the coefficient of variation of the printed biomolecular droplet is 38.4, when a magnet does not exist, an average diameter of the printed biomolecular droplet is 129.7 µm and the coefficient of variation of the printed biomolecular droplet is 34.9, in the case of 3% of an aqueous glycerol solution, an average diameter of the biomolecular droplet is 111.9 µm and the coefficient of variation of the biomolecular droplet is 26.3, and in the case of 3% of an aqueous glycerol solution including $6.7 \times 10^8$ beads/ml of Dynabeads M-280 streptavidin (diameter: 2.8 µm), an average size of the biomolecular droplet is 52.2 µm and the coefficient of variation of the biomolecular droplet is 23.5. From these results, it is confirmed that a micro bead which is not magnetic is used it can not produce a biomolecular droplet with a volume as small as that produced using an exemplary embodiment of a micro magnetic bead according to the present invention. In the current example of the present invention, a surface of the substrate is evenly formed, and only one target surface is formed on the substrate.

Figure 17:
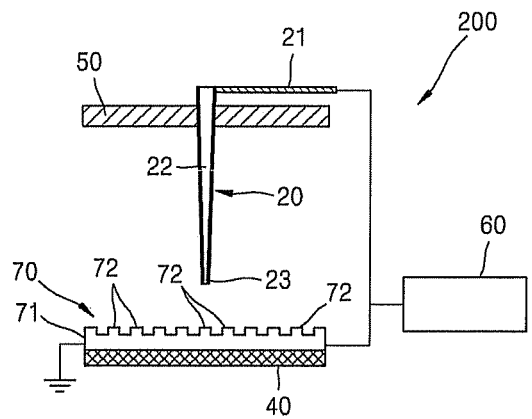
FIG. 17 is a schematic cross-sectional view of another exemplary embodiment of a printing device according to the present invention.
Figure 19:
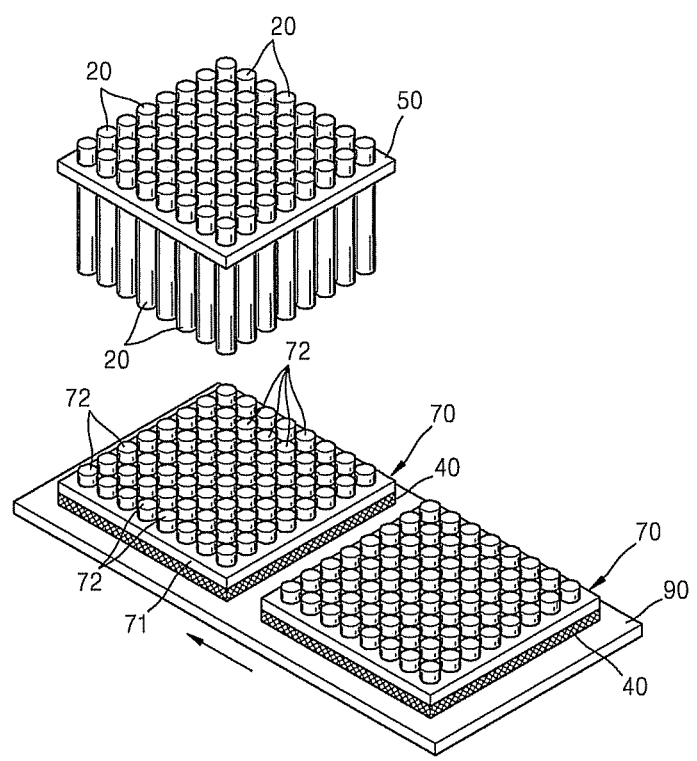
FIG. 19 is a schematic diagram for illustrating an exemplary embodiment of a process of consecutively printing biomolecular droplets on a plurality of silicon substrates using the exemplary embodiment of a printing device of FIG. 17, according to the present invention.

FIG. 17 is a schematic cross-sectional view of another exemplary embodiment of a printing device 200 for printing biomolecular droplets according to the present invention. Referring to FIG. 17, a plurality of protrusions 72 can be formed on the surface of a substrate 70 and the protruding parts 72 can be target surfaces. As illustrated in FIG. 17, the substrate 70 may include a planar part 71 and the protrusions 72 protrude upwards from the planar part 71. The protrusions 72 are disposed with substantially the same pitch. Each of the protrusions 72 is a target surface on which a biomolecular droplet ejected from a nozzle 23 of an electric field forming electrode 20 is deposited. In addition, the substrate 70 is placed on a stage 90 as illustrated in FIG. 19, and the stage 90 can be moved by a conveyor, or other similar device.

In the apparatus 200 for printing a biomolecular droplet on the substrate 70 using the electric charge concentration effect, a separate driving device is driven to dispose the electric field forming electrode 20 above the protrusions 72 to be printed, and thus a printer body 50 disposed above the nozzle 23 of the electric field forming electrode 20 is moved. Then, a DC voltage and an AC voltage are applied to the electric field forming electrode 20 to eject the biomolecular droplet 10 onto the protrusions 72 of the substrate 70. The driving device is driven again to move the printer body 50, and thus the electric field forming electrode 20 is disposed above another protrusion 72 and the DC voltage and the AC voltage are applied to the electric field forming electrode 20 again to print the biomolecular droplet. Using such a method, the biomolecular droplet 10 is ejected with respect to a plurality of the protrusions 72 by moving the printer body 50.

When a fragment of a target DNA to be analyzed is bound to the biochip or DNA microarray manufactured by printing the biomolecular droplet 10 on all of the protrusions 72 as described above, a hybridization bond formed on each protrusion 72 can be observed using an optical method or a radioactive chemical method, since the protrusions 72 are separated from each other by a denting portion. Accordingly, a base sequence of the target DNA can be more accurately analyzed.

Figure 18:
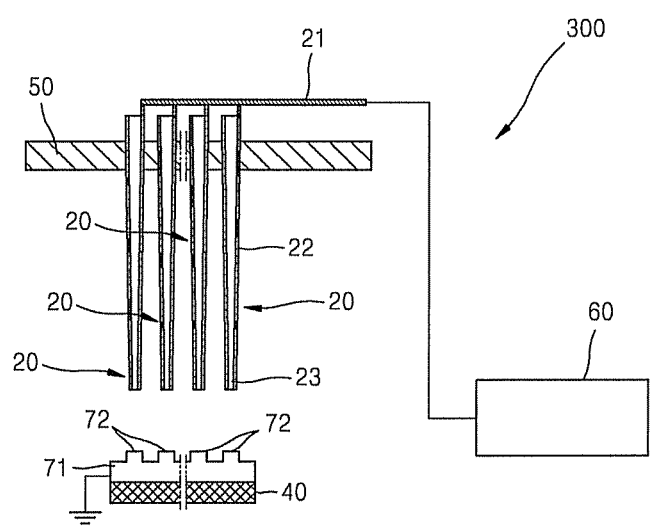
FIG. 18 is a schematic cross-sectional view of another exemplary embodiment of a printing device according to the present invention.

Meanwhile, according to the current previous exemplary embodiment of the present invention illustrated in FIG. 17, only one electric field forming electrode 20 is used to print the biomolecular droplet 10 on each protrusion 72 of the substrate 70. However, a plurality of electric field forming electrodes 20 can be arranged to correspond to each of a plurality of protrusions 72 of a substrate 70 as illustrated in FIG. 18. FIG. 18 is a schematic cross-sectional view of another exemplary embodiment of a printing device 300 for printing biomolecular droplets, according to the present invention. The electric field forming electrodes 20 as illustrated in FIG. 18 are disposed at substantially the same pitch with respect to the protrusions 72 of the substrate 70, and thereby each protrusion 72 corresponds to one electric field forming electrode 20. Each of the electric field forming electrodes 20 is electrically insulated. In addition, each of the electric field forming electrodes 20 is electrically connected to an electrode lead wire 21, and the electrode lead wire 21 is electrically connected to an open circuit type voltage applying unit 60. Accordingly, when the open circuit type voltage applying unit 60 is driven, voltage is applied to all of the electric field forming electrodes 20.

In the exemplary embodiment of an apparatus 300 for printing biomolecular droplets on the substrate 70 using the electric charge concentration effect, it is particularly useful when different kinds of biomolecular droplets are simultaneously printed. FIG. 19 is a schematic diagram for illustrating an exemplary embodiment of a process of consecutively printing biomolecular droplets on a plurality of silicon substrates 70 using the printing device 200 of FIG. 17, according to the present invention, and illustrates a process of manufacturing several pieces of silicon substrates, that is, biochips or DNA microarrays using the electric charge concentration effect. As illustrated in FIG. 19, when printing of a biomolecular droplet on one silicon substrate 70 is terminated, a stage 90 supporting the silicon substrate 70 is moved, thereby printing a biomolecular droplet on another silicon substrate 70.

According to the current embodiment of the present invention, the printer body 50 is included, however the printer body 50 may be omitted.

In addition, according to the current exemplary embodiment of the present invention, an AC voltage and a DC voltage are simultaneously applied to the electric field forming electrode 20, however it is possible that either only the AC voltage or only the DC voltage is applied thereto.

In addition, according to the current exemplary embodiment of the present invention, a positive charge is migrated in the biomolecular droplet and a negative charge is induced in the substrate 70. However, a negative charge may be migrated in the biomolecular droplet so that a positive charge is induced by the negative charge in a portion of the substrate 70 disposed opposite the biomolecular droplet. Irrespective of where the positive and negative charges are formed, a force between the negative charge and the positive charge is generated, thus causing the biomolecular droplet to be ejected onto the substrate 70.

According to the current exemplary embodiment of the present invention, the substrate 70 includes a planar part 71 and a plurality of protrusions 72, however the substrate 70 can omit the protrusions 72.

According to an exemplary embodiment of the present invention, a magnet 40 is disposed on, or is adjacent to, a bottom surface of the substrate 70 which has substantially the same size as that of the planar part 71 of the substrate 70, however the magnet 40 can have any shape provided it applies a magnetic force to a micro magnetic bead included in the biomolecular droplet existing in an accommodating area of the electric field forming electrode 20 to attract the micro magnetic bead towards the substrate 70.

According to tan exemplary embodiment of the present invention, a force acts on the biomolecular droplet suspended from the nozzle 23 by the electric charge concentration effect, and also the biomolecular droplet suspended from the nozzle 23 is tapered by magnetic micro beads concentrated at a lowest point of the biomolecular droplet in the presence of magnetic micro beads and the magnet 40, and thus a lower portion of the biomolecular droplet becomes narrower. Therefore, a biomolecular droplet with a smaller volume and diameter than those of a biomolecular droplet in the prior art can be ejected onto the target surface of the substrate 70. Accordingly, printing of a large number of biomolecular droplets on the substrate 70 is possible, and manufacturing a biochip having a high density is also made easier. In addition, according to the present invention, since a biomolecular droplet having a low density of cells, e.g., 6 or fewer cells, per biomolecular droplet can be manufactured, it is particularly useful in a study of interaction of cells. This may be particularly useful in studies including a stem cell.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for printing a biomolecular droplet onto a substrate using an electric charge concentration effect, the apparatus comprising:
an electric field forming electrode which comprises an accommodating area in which a biomolecular droplet comprising micro magnetic beads and biomolecules is accommodated and a nozzle formed on an end of the accommodating area through which the biomolecular droplet is discharged;
a grounded substrate disposed below the electric field forming electrode, which comprises a target surface onto which the biomolecular droplet discharged from the nozzle of the electric field forming electrode is deposited;
a magnet disposed below the substrate which applies a magnetic force on the micro magnetic beads; and
an open circuit type voltage applying unit electrically connected to the electric field forming electrode which applies a charge to the electric field forming electrode which generates an electrical force which causes the biomolecular droplet to be ejected onto the target surface of the substrate due to a force generated by the charge in the electric field forming electrode and a charge induced on the substrate by the charge in the electric field forming electrode,
wherein the biomolecular droplet suspended from the nozzle is tapered and has a lower portion with reduced width in which micro magnetic beads are concentrated with the biomolecules at a lowest point in the biomolecular droplet, and has a smaller size and volume, than that of a biomolecular droplet without micro magnetic beads, and wherein the biomolecular droplet so printed on a substrate has a smaller size than that of a biomolecular droplet printed without micro magnetic beads.

2. The apparatus of claim 1, wherein the magnet is adjacent to a lower surface of the substrate.

3. The apparatus of claim 1, wherein a diameter of the micro magnetic beads is about 100 nm to about 15,000 nm.

4. The apparatus of claim 1, wherein the concentration of micro magnetic beads in each biomolecular droplet is between about 104 beads/ml to about 1012 beads/ml.

5. The apparatus of claim 1, wherein the biomolecules are selected from the group consisting of nucleic acids, proteins, oligopetides, saccharides, eukaryotic cells, stem cells, viruses and bacteria.

6. The apparatus of claim 1, wherein the biomolecular droplet printed on the substrate has a diameter of about 60 μm or less.

7. The apparatus of claim 1, further comprising a printer body which supports the electric field forming electrode.

8. The apparatus of claim 1, wherein the electric field forming electrode and the open circuit type voltage applying unit are electrically connected to an electrode lead wire which is connected to a top end of the electric field forming electrode.

9. The apparatus of claim 1, wherein the open circuit type voltage applying unit simultaneously applies an AC voltage and a DC voltage to the electric field forming electrode.

10. The apparatus of claim 9, wherein the DC voltage is in the range of about 5 V to about 100,000 V and the AC voltage is in the range of about 5 V to about 100,000 V.

11. The apparatus of claim 10, wherein the DC voltage is in the range of about 500 V to about 10,000 V and the AC voltage is in the range of about 500 V to about 10,000 V.

12. The apparatus of claim 10, wherein the AC voltage has a frequency of about 10 Hz to about 1,000 Hz.

13. The apparatus of claim 12, wherein the DC voltage has a voltage of about 2,000 V and the AC voltage has a voltage of about 500 V and a frequency of about 130 Hz.

14. The apparatus of claim 1, wherein the substrate is made of at least one selected from the group consisting of silicon, glass, and polymer.

15. The apparatus of claim 14, wherein a surface of the substrate is coated with at least one selected from the group consisting of an amine group, a carboxyl group, biotin, streptavidin, poly-L-lysine and thiol.

16. The apparatus of claim 1, wherein the substrate comprises a planar part, and a plurality of protrusions protruding upwards from the planar part.

17. The apparatus of claim 16 wherein the protrusions comprise a target surface of the substrate.

18. The apparatus of claim 1, wherein the target surface of the substrate is disposed below and substantially perpendicular to the electric field forming electrode such that the nozzle of the electrode faces the target surface.

19. The apparatus of claim 1, wherein the electric field forming electrode is made of at least one selected from the group consisting of a conductive metal, a conductive polymer and indium tin oxide glass.

20. The apparatus of claim 1, wherein at least a portion of the nozzle of the electric field forming electrode is hydrophobically treated.

21. The apparatus of claim 1, wherein the electric field forming electrode is needle shaped.

22. A method of printing a biomolecular droplet on a substrate using an electric charge concentration effect, the method comprising:
   disposing an electric field forming electrode comprising an accommodating area in which the biomolecular droplet comprising micro magnetic beads and biomolecules is accommodated and a nozzle formed at an end of the accommodating area through which the biomolecular droplet is discharged above the substrate;
   disposing the substrate below the electric field forming electrode, wherein the substrate is grounded and comprises a target surface onto which the biomolecular droplet discharged from the nozzle of the electric field forming electrode is deposited;
   disposing a magnet which applies a magnetic field to the micro magnetic beads below the substrate;
   electrically connecting an open circuit type voltage applying unit to the electric field forming electrode to build a charge in the electric field forming electrode;
   supplying the biomolecular droplet comprising the micro magnetic beads and biomolecules to the accommodating area of the electric field forming electrode; and
   ejecting the biomolecular droplet onto the target surface when the open circuit type voltage applying unit applies a voltage to the electric field forming electrode due to a force generated by the charge in the electric field forming electrode and a charge induced on the substrate by the charge in the electric field forming electrode,
   wherein the biomolecular droplet suspended from the nozzle is tapered and has a lower portion with reduced width in which micro magnetic beads are concentrated with the biomolecules at a lowest point in the biomolecular droplet, and has a smaller size and volume, than that of a biomolecular droplet without micro magnetic beads, and
   wherein the biomolecular droplet so printed on a substrate has a smaller size than that of a biomolecular droplet printed without micro magnetic beads.

23. The method of claim 22, further comprising:
   culturing cells adherently on the substrate after the biomolecular droplet is ejected;
   removing the magnet;
   removing the micro magnetic beads by washing the adherently cultured cells; and
   adding a fresh medium onto the adherently cultured cells.

24. An apparatus for printing biomolecular droplets onto a substrate using an electric charge concentration effect, the apparatus comprising:
   a plurality of electric field forming electrodes arranged with substantially the same pitch, wherein each electric field forming electrode comprises an accommodating area in which a biomolecular droplet comprising micro magnetic beads and biomolecules is accommodated and a nozzle formed on an end of the accommodating area through which the biomolecular droplet is discharged;
   a grounded substrate disposed below the plurality of electric field forming electrodes, which comprises a plurality of target surfaces arranged on the substrate onto which the biomolecular droplets discharged from the nozzles of the electric field forming electrodes are deposited, wherein each of the target surfaces are disposed to correspond to an electric field forming electrode;
   a magnet disposed below the substrate which applies a magnetic force on the micro magnetic beads; and
   an open circuit type voltage applying unit electrically connected to the electric field forming electrodes which applies a charge to each electric field forming electrode which generates an electrical force which causes the biomolecular droplets to be ejected onto the target surfaces of the substrate due to a force generated by the charge in the electric field forming electrodes and a charge induced on the substrate by the charge in the electric field forming electrodes,
   wherein the biomolecular droplets suspended from the nozzles are tapered and have a lower portion with reduced width in which micro magnetic beads are concentrated with the biomolecules at a lowest point in the biomolecular droplets, and have a smaller size and volume, than that of a biomolecular droplet without micro magnetic beads, and wherein the biomolecular droplets so printed on a substrate have a smaller size than that of a biomolecular droplet printed without micro magnetic beads.

* * * * *